US011925702B2

(12) United States Patent
Kim et al.

(10) Patent No.: US 11,925,702 B2
(45) Date of Patent: Mar. 12, 2024

(54) METHODS FOR EXTRACTING COMPOUND FROM GINSENG, GINSENG EXTRACT COMPRISING THE COMPOUND AND COMPOSITION FOR ENHANCING SKIN BARRIER COMPRISING THE SAME

(71) Applicant: AMOREPACIFIC CORPORATION, Seoul (KR)

(72) Inventors: Dong Hyun Kim, Yongin-si (KR); Sehyun Kim, Yongin-si (KR); Hyunsoo Kim, Yongin-si (KR); Misook Shin, Yongin-si (KR); Seung Jo Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 18/169,522

(22) Filed: Feb. 15, 2023

(65) Prior Publication Data
US 2023/0381091 A1    Nov. 30, 2023

(30) Foreign Application Priority Data

May 31, 2022    (KR) .................... 10-2022-0067017

(51) Int. Cl.
*A61K 36/00*    (2006.01)
*A61K 8/9789*    (2017.01)
*A61Q 19/00*    (2006.01)

(52) U.S. Cl.
CPC ............ *A61K 8/9789* (2017.08); *A61Q 19/00* (2013.01); *A61K 2800/85* (2013.01)

(58) Field of Classification Search
CPC ................................................. A61K 2800/85
See application file for complete search history.

(56) References Cited

U.S. PATENT DOCUMENTS 8,735,129 B2    5/2014   An et al.

FOREIGN PATENT DOCUMENTS

| CN | 102302529 B | 8/2013 | |
|---|---|---|---|
| CN | 113841888 A | 12/2021 | |
| JP | 5748256 B1 * | 7/2015 | ........... A61K 31/704 |
| JP | 6209304 B2 | 10/2017 | |
| KR | 10-2011-0107159 A | 9/2011 | |
| KR | 10-2013-0134930 A | 12/2013 | |
| KR | 10-2015-0057664 A | 5/2015 | |
| KR | 10-2017-0037768 A | 4/2017 | |
| KR | 10-2018-0085239 A | 7/2018 | |
| KR | 10-2019-0091164 A | 8/2019 | |
| WO | 2016/035182 A1 | 3/2016 | |

OTHER PUBLICATIONS

Chai et al., Analysis of volatile components of fermented Panax ginseng by HS-SPME/GC-MS. Shipin Yanjiu Yu Kaifa (2016), 37(22), 162-168 (Year: 2016).*
"Article 4 of the Regulations for Regulation on the Standards of Natural and Organic Cosmetics, and the Enforcement of Table 5", Jul. 29, 2019. 6 pgs.
Korean Written Decision on Registration issued in KR Application No. 10-2022-0067017 dated Aug. 2, 2022.
Korean Preliminary Examination Result Notice issued in KR Application No. 10-2022-0067017 dated Jul. 4, 2022.
Yu Fu, "Biotransformation of ginsenoside Rb1 to Gyp-XVII and minor ginsenoside Rg3 by endophytic bacterium *Flavobacterium* sp. GE32 isolated from *Panax ginseng*", Letter Appl. Microbiology, vol. 68, No. 2, Feb. 28, 2019, 23 pages (pp. 6/31-28/31).
Communication dated Sep. 22, 2023 issued by the State Intellectual Property of the P.R.China in application No. 202310406009.1.
Communication dated Nov. 6, 2023 issued by the European Patent Office in application No. 23162425.5.

* cited by examiner

*Primary Examiner* — Qiuwen Mi
(74) *Attorney, Agent, or Firm* — Sughrue Mion, PLLC

(57) ABSTRACT

Disclosed are a method for extracting a compound represented by Chemical Formula 1 from ginseng, including anaerobic natural fermentation of ginseng, an anaerobic-naturally fermented ginseng extract including the compound represented by Chemical Formula 1 extracted by the method, and a method of enhancing the skin barrier including applying a composition including an effective amount of the anaerobic-naturally fermented ginseng extract.

[Chemical Formula 1]

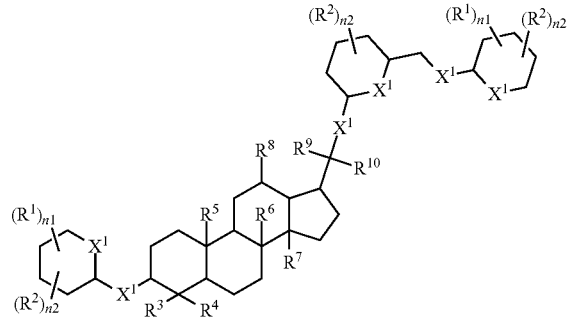

In Chemical Formula 1, each substituent is as defined in the specification.

6 Claims, 7 Drawing Sheets

METHODS FOR EXTRACTING COMPOUND FROM GINSENG, GINSENG EXTRACT COMPRISING THE COMPOUND AND COMPOSITION FOR ENHANCING SKIN BARRIER COMPRISING THE SAME

CROSS-REFERENCE TO RELATED APPLICATION

This application claims priority to and the benefit of Korean Patent Application No. 10-2022-0067017 filed in the Korean Intellectual Property Office on May 31, 2022, the entire contents of which are incorporated herein by reference.

BACKGROUND OF THE INVENTION

(a) Field of the Invention

This disclosure relates to a method for extracting a compound from ginseng, a ginseng extract including the compound, and a composition for enhancing a skin barrier including the same.

(b) Description of the Related Art

Korean ginseng (*Panax ginseng* C. A. Meyer), native to the Korean Peninsula and northeast China, is a perennial plant belonging to the genus Araliaceae and is in the ginseng family and called 'Ginseng' in English, which is derived from the Chinese pronunciation of ginseng. *Ginseng* has been used as a traditional herbal plant for thousands of years in Asian countries such as Korea, China, and Japan, and recently is being consumed worldwide. *Ginseng* sprouts from the roots in the ground every spring, and leaves and stems thereof wither and die in autumn. In addition, since ginseng is a semi-shady plant, the aerial parts are withered when exposed to direct sunlight, as chlorophyll of the leaves is destroyed. *Ginseng* mostly starts to bloom in March and fully blooms by mid-May. In summer, ginseng is shaded to prevent the weak aerial parts from withering by direct sunlight in ginseng farms and harvested from mid-July to late July. Raw ginseng (fresh ginseng) produced in Korea is consumed as fresh ginseng, root ginseng (white ginseng, red ginseng, *Taegeuk ginseng*, black ginseng), and processed ginseng products. The fresh ginseng is raw ginseng harvested from the field and contains about 70% to about 80% of moisture and thus is classified according to a method of removing the moisture into white ginseng, red ginseng, *Taegeuk ginseng*, or black ginseng. Due to an increase in labor costs according to a decrease in Korean domestic ginseng farmers and a limitation of mass production according to small farming areas, Korean ginseng's global share is declining, which requires development of high-quality and expensive ginseng differentiated from the others and scientific farming.

Research on ginseng began in 1845 when Garriques of the United States separated an amorphous glycoside mixture from western ginseng and named it 'panaquilon'. However, since Brekhman, a former Soviet pharmacologist, announced saponin as an active ingredient of ginseng in 1957, saponin has been focused on in many studies. Saponin, which is derived from a Spanish word 'foam,' is well soluble in water and alcohol and has continuous foam, and physiologically, is known to have detoxification and red blood cell hemolysis effects. Chemically, saponin is colored red by a Libermann-Buchard reaction and a glycoside in which saccharides are linked to aglycone (sapogenin, aglycone). In 1960, when a chemical structure of ginseng saponin was clarified by Shibata and the like, research on the ginseng saponin started to be accelerated.

Ginsenoside, a saponin component of ginseng, means a glycoside contained in the ginseng, and as 31 chemical structures so far have been clarified, and is classified into protopanaxadiol (PPD) and protopanaxatriol (PPT), which are triterpenoids of dammarane family, according to the structural characteristics. Ginsenoside is saponin found in ginseng, of which a content mainly determines quality of ginseng. Ginsenoside is a main pharmacologically active ingredient of ginseng, means a glycoside separated from ginseng, and has a structure of glycone and aglycone (sapogenin). Ginsenoside is called Rx, wherein 'R' means 'root,' and 'x' is called o, a, b, c, d, e, f, g, h, and the like in order according to a location of Rf values obtained by dividing a distance traveled by a sample by a distance traveled by a solvent when a ginseng extract is separated on TLC. Ginsenoside may be classified into PPD, PPT, ocotillol-type, and oleanolic acid according to four aglycone structures. Protopanaxadiol (PPD)-based saponins include ginsenoside Rb1, Rb2, Rc, Rd, Rg3, and the like, and protopanaxatriol (PPT)-based saponins include ginsenoside Re, Rg1, Rg2, Rh1, and the like.

Pharmacological action and efficacy of ginseng known so far have been reported to include anti-diabetic activity, anti-cancer action, antioxidant action, anti-arteriosclerosis action, anti-stress action, brain activity promotion action, anti-inflammatory activity, allergic disease treatment, promotion of protein synthesis ability, etc.

*Ginseng* is steamed with vapor and the like and dried for long term storage, to produce red ginseng. Since the steaming and drying promote a browning reaction of ginseng, red ginseng looks light brown to reddish brown and becomes more digestible than white ginseng, because starch particles in ginseng tissues are gelatinized during the steaming. In addition, since various enzymes are inactivated, red ginseng is more stable than white ginseng during the storage, and in addition, new physiologically active components, which are not present in fresh ginseng or white ginseng, are produced through some chemical transformations during the manufacturing of red ginseng. These specific components of red ginseng are representatively ginsenoside Rg2, Rg3, Rh1, and Rh2. Ginsenoside Rg2 has been reported to have an antagonistic action against cancer toxins and an inhibitory action on tumor angiogenesis, and dinsenoside Rg3 has been reported to inhibit cancer cells from invasion into normal cells and angiogenic metastasis. In addition, ginsenoside Rh1 has an effect of protecting brain nerve cells and improving learning ability, and Rh2 is known to inhibit proliferation of cancer cells and induce their differentiation into morphologically and functionally normal cells, which draws attentions as unique features of red ginseng. As aforementioned, as pharmacological action and efficacy of the specific component of ginseng have been proven, recent red ginseng-related research has been more reported on instrumental analysis studies such as medicine development by using red ginseng components, chemical structure identification of ginsenoside which is a main active ingredient of ginseng, separation of substances, and the like, and on an increase in a content of red ginseng.

An extraction is an essential process to obtain many physiologically active ingredients from natural products and a first step of separation and purification processes to obtain specific active ingredients. A common extraction method used in the food, pharmaceutical, and cosmetic industries includes steam distillation, reflux cooling extraction, ultrasonic extraction (UAE), supercritical fluid extraction (SFE), microwave-assisted extraction (MAE), accelerated solvent extraction (ASE, PLE), high hydrostatic pressure extraction (HHP), and the like.

The microwave-assisted extraction has been reported in the studies using pigment extraction from paprika, antioxidant component extraction from raspberries, saponin extraction from ginseng, etc. with a microwave extractor, and the acceleration solvent extraction has been reported to be used for various extractions including functional component extraction from saxifrage, lignan extraction from *Schisandra chinensis*, carotenoids and chlorophyll pigment extraction from chlorella, and the like by using an accelerated solvent extractor. On the other hand, the acceleration solvent extraction [about 70% ethanol, about 2000 psi, about 150° C.] for extracting specific ginsenoside extracts (Rb1+Rg1+Rg3, etc.) of red ginseng exhibits a yield of about 145.24 mg/100 g DW, and in both ginseng and red ginseng, compared with hot water extraction (about 95° C., about 1 hour), the high hydrostatic pressure extraction (HHP) (about 80 MPa, about 30° C., about 12 hours) has been reported to exhibit about 1.2 to about 1.4 times higher extraction content of ginsenoside, an active ingredient. In addition, a method of doubling the extraction yield of ginsenoside by combining ultra-high pressure equipment and an enzyme treatment has been reported, and Rd, a specific component of ginsenoside has been reported to be about 7 times more extracted, when extracted for about 24 hours with a specific combination of enzymes (about 2 U/mL of Cellulase+about 4 U/ml of Cellobiase) added in the high hydrostatic pressure (HHP)-enzyme treatment extraction, compared with when extracted with the enzyme treatment alone under atmospheric pressure. Korean wild ginseng has main physiologically active ingredients such as ginsenoside glycosides and products of the glycosides hydrolyzed by acids such as a protopanaxadiol group, a protopanaxatriol group, and oleanolic acid. In this way, the active ingredients of ginseng such as ginsenoside may be extracted in various extraction methods, but since a yield or activity thereof may vary depending on the extraction methods, an appropriate extraction method is very important to adopt for the purpose.

On the other hand, the present inventors have been continuously conducting related research for a very long time in order to develop cosmetic compositions from natural and organic raw materials, and particularly, have repeatedly studied, in many ways, what excellent effects fermented ginseng extracts have, compared with conventional unfermented ginseng extracts, and as a result, discovered a method of extracting a specific type of ginsenoside compound in a high content from fermented ginseng, in particular, under an anaerobic condition, and confirmed that a composition including the compound extracted in this method as an active ingredient has a very excellent effect of enhancing skin barriers and an advantage for skin moisturizing, etc., completing the present invention.

SUMMARY OF THE INVENTION

An embodiment provides a method for extracting a specific compound from ginseng by anaerobic natural fermentation of ginseng.

Another embodiment provides an anaerobic-naturally fermented ginseng extract including a specific compound extracted by the aforementioned method.

Another embodiment provides a composition for enhancing a skin barrier including the anaerobic-naturally fermented ginseng extract as an active ingredient.

According to an embodiment, provided is a method for extracting a compound represented by Chemical Formula 1 from ginseng, including anaerobic natural fermentation of ginseng.

[Chemical Formula 1]

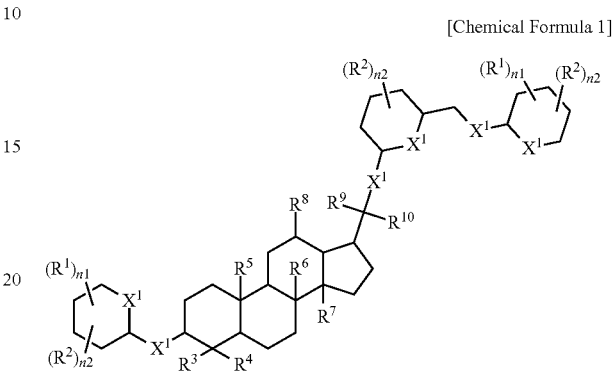

In Chemical Formula 1, $X^1$ is an oxygen atom or a sulfur atom, $R^1$ to $R^{10}$ are each independently a hydroxy group or a substituted or unsubstituted C1 to C20 alkyl group, and n1 and n2 are each independently an integer of 0 to 4, provided that $1 \le n1+n2 \le 4$.

The natural fermentation may be fermentation for about 15 days to about days at about 35° C. to about 65° C.

The natural fermentation may be fermentation of the ginseng in a sealed state.

The ginseng may be subjected to rolling.

The rolling may be performed for about 20 minutes to about 60 minutes. The method may include: washing ginseng; rolling the washed ginseng; cutting and/or crushing the rolled ginseng; naturally fermenting the cut and/or crushed ginseng; and drying the naturally fermented ginseng.

The ginseng may include fresh ginseng.

In Chemical Formula 1, $R^1$ may be a C1 to C20 alkyl group substituted with a hydroxy group, $R^2$ and $R^8$ may each independently be a hydroxy group, $R^3$ to $R^7$ and $R^9$ may each independently be an unsubstituted C1 to C20 alkyl group, and $R^{10}$ may be a C1 to C20 alkyl group substituted with a functional group represented by Chemical Formula 2,

[Chemical Formula 2]

wherein, in Chemical Formula 2, $L^1$ may be a substituted or unsubstituted C1 to C20 alkylene group, $R^{11}$ and $R^{12}$ may each independently be a hydrogen atom or a substituted or unsubstituted C1 to C20 alkyl group, n1 may be an integer of 1, and n3 may be an integer of 3.

Chemical Formula 1 may be represented by Chemical Formula 1-1.

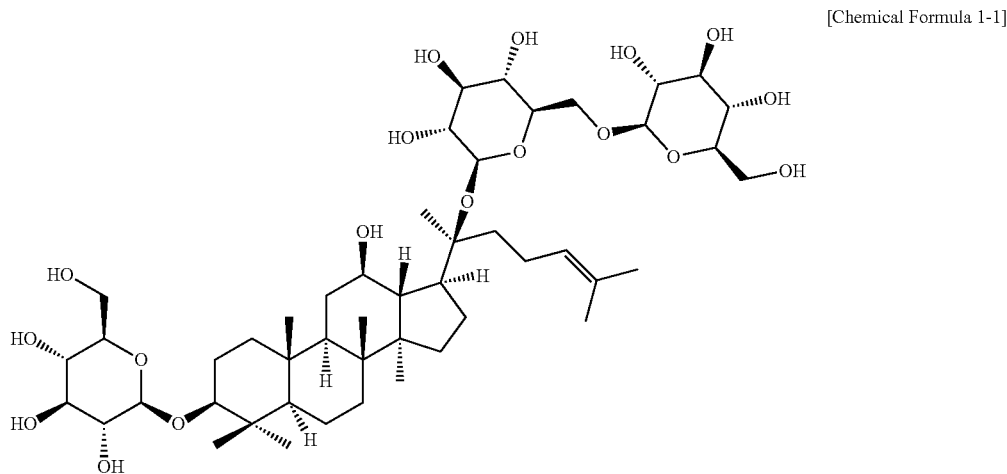

[Chemical Formula 1-1]

According to another embodiment, an anaerobic-naturally fermented ginseng extract includes the compound represented by Chemical Formula 1 extracted by the aforementioned method.

According to another embodiment, a method of enhancing the skin barrier includes applying a composition including an effective amount of the anaerobic-naturally fermented ginseng extract to the skin.

The anaerobic-naturally fermented ginseng extract may be included in a concentration range of about 1 μg/ml to about 100 mg/ml based on the total amount of the composition.

The compound represented by Chemical Formula 1 may be included in a concentration range of about 50 nmole to about 5000 nmole based on the total amount of the composition.

According to another embodiment, a use of the anaerobic-naturally fermented ginseng extract for enhancing the skin barrier is provided.

In the conventional fermentation of ginseng, in most cases, ginseng is fermented using specific microorganisms that do not exist in ginseng. However, in an embodiment, by fermenting ginseng using microorganisms present in ginseng itself, the content of ginsenoside compounds represented by a specific chemical formula in fermented ginseng may be greatly increased, and therefore, it is also possible to extract a high content of the ginsenoside compound represented by the above specific chemical formula.

In addition, a composition including this as an active ingredient may impart an excellent moisturizing effect to the skin by having a skin barrier enhancing function.

DETAILED DESCRIPTION OF THE EMBODIMENTS

Figure 1:
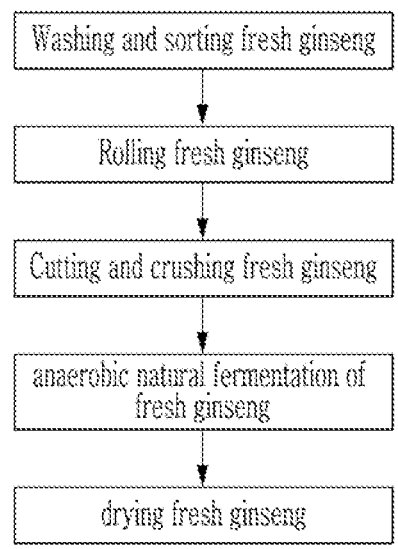
FIG. 1 is a flowchart of a method according to an embodiment.

Hereinafter, example embodiments of the present invention will be described in detail. However, these example embodiments are only examples and do not limit the present invention. However, this disclosure may be embodied in many different forms and is not construed as limited to the example embodiments set forth herein.

As used herein, when specific definition is not otherwise provided, "substituted" refers to replacement of at least one hydrogen of a functional group of the present invention by at least one substituent selected from a halogen atom (F, Br, Cl, or I), a hydroxy group, a nitro group, a cyano group, an amino group ($NH_2$, $NH(R^{200})$, or $N(R^{201})(R^{202})$, wherein $R^{200}$, $R^{201}$, and $R^{202}$ are the same or different and are each independently a C1 to C10 alkyl group), an am idino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group, and a substituted or unsubstituted heterocyclic group.

As used herein, when specific definition is not otherwise provided, "alkyl group" refers to a C1 to C20 alkyl group, and specifically a C1 to C15 alkyl group, "cycloalkyl group" refers to a C3 to C20 cycloalkyl group, and specifically a C3 to C18 cycloalkyl group, "alkoxy group" refers to a C1 to C20 alkoxy group, and specifically a C1 to C18 alkoxy group, "aryl group" refers to a C6 to C20 aryl group, and specifically a C6 to C18 aryl group, "alkenyl group" refers to a C2 to C20 alkenyl group, and specifically a C2 to C18 alkenyl group, "alkylene group" refers to a C1 to C20 alkylene group, and specifically a C1 to C18 alkylene group, and "arylene group" refers to a C6 to C20 arylene group, and specifically a C6 to C16 arylene group.

As used herein, when a definition is not otherwise provided, the term "combination" refers to mixing or copolymerization. Also, "copolymerization" refers to block copolymerization or random copolymerization, and "copolymer" refers to a block copolymer or a random copolymer.

One aspect of the present disclosure relates to a natural fermentation technology using microorganisms possessed by ginseng itself, without inoculation of specific microorganisms, and a method for extracting a compound represented by Chemical Formula 1 from ginseng using the same.

[Chemical Formula 1]

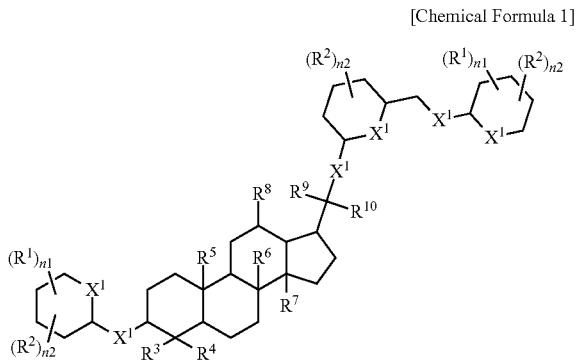

In Chemical Formula 1,
$X^1$ is an oxygen atom or a sulfur atom,
$R^1$ to $R^{10}$ are each independently a hydroxy group or a substituted or unsubstituted C1 to C20 alkyl group, and
n1 and n2 are each independently an integer of 0 to 4, provided that $1 \leq n1+n2 \leq 4$.

The natural fermentation may refer to fermentation that spontaneously occurs rather than is artificially caused by using yeast or the like. The fermentation using yeast is the same as conventional fermenting by inoculating specific microorganisms into ginseng, which may not increase a content of a specific ginsenoside compound represented by Chemical Formula 1.

However, the natural fermentation may be anaerobic natural fermentation under an anaerobic condition. Herein, compared with aerobic natural fermentation under an aerobic condition, a content of the specific ginsenoside compound represented by Chemical Formula 1 in ginseng may be selectively significantly increased.

The anaerobic fermentation may refer to a process in which anaerobic microorganisms growing without oxygen decompose and ferment a substrate in the absence of oxygen, while the aerobic fermentation may refer to a process in which aerobic microorganisms growing with oxygen decompose and ferment a substrate in the presence of oxygen.

The anaerobic fermentation is the same as anoxic conditions in that oxygen is not present, but since neither oxygen nor combined oxygen is present in the anaerobic fermentation, while combined oxygen such as nitric acid is present in the anoxic conditions, the anaerobic fermentation may differ from the anoxic conditions. In other words, the anaerobic fermentation in an embodiment refers to a condition in which neither oxygen nor combined oxygen is present. (When ginseng is naturally fermented under the anoxic conditions in which the combined oxygen is present, the content of the specific ginsenoside compound represented by Chemical Formula 1 is difficult to selectively increase.)

For example, the (anaerobic) natural fermentation may be performed at greater than or equal to about 35° C., for example greater than or equal to about 40° C., for example greater than or equal to about 45° C., for example greater than or equal to about 50° C., for example less than or equal to about 65° C., for example less than or equal to about 60° C., for example less than or equal to about 55° C., for example less than or equal to about 50° C., for example about ° C. to about 65° C., for example about 40° C. to about 60° C., or for example about 45° C. to about 55° C. for example greater than or equal to about 15 days, for example greater than or equal to about 16 days, for example greater than or equal to about 17 days, for example greater than or equal to about 18 days, for example greater than or equal to about 19 days, for example greater than or equal to about 20 days, for example greater than or equal to about 21 days, for example less than or equal to about 30 days, for example less than or equal to about 29 days, for example less than or equal to about 28 days, for example less than or equal to about 27 days, for example less than or equal to about 26 days, for example less than or equal to about 25 days, for example less than or equal to about 24 days, for example less than or equal to about 23 days, for example less than or equal to about 22 days, for example less than or equal to about 21 days, for example about 15 days to about 30 days, for example about 16 days to about 28 days, for example about 17 days to about 26 days, for example about 18 days to about 24 days, for example about 19 days to about 22 days, or for example about 20 days to about 21 days. When the (anaerobic) natural fermentation is performed under the temperature and time conditions, the content of the specific ginsenoside compound represented by Chemical Formula 1 in ginseng may be significantly increased.

The (anaerobic) natural fermentation may be fermented in a state of sealing the ginseng. The sealing is to age (anaerobically) naturally fermented ginseng, wherein the content of the specific ginsenoside compound represented by Chemical Formula 1 may be significantly increased, compared with (anaerobically) naturally fermented ginseng without the sealing.

For example, the ginseng may be rolled ginseng. The rolling may be a process of repeatedly rubbing (breaking cell tissues and cell walls) ginseng and ginseng roots with a physical force. When the rolled ginseng is (anaerobically) naturally fermented, compared with when unrolled ginseng is (anaerobically) naturally fermented, the content of the specific ginsenoside compound represented by Chemical Formula 1 in the ginseng may be increased.

For example, the rolling may be performed for about 20 minutes to about minutes. For example, the rolling may be a process of rubbing at least about 60 kg of washed ginseng (i.e., greater than or equal to about 20 kg of ginseng) for about 20 minutes to about 60 minutes, for example about 20 minutes to about 50 minutes, or for example about 20 minutes to about 40 minutes, by using a physical force.

When the rolling process is performed under the conditions, the content of the specific ginsenoside compound represented by Chemical Formula 1 in the ginseng may be significantly increased.

For example, the method may include: washing ginseng; rolling the washed ginseng; cutting and/or crushing the rolled ginseng; naturally fermenting the cut and/or crushed ginseng; and drying the naturally fermented ginseng (refer to FIG. 1).

For example, the drying may be hot air drying. For example, the drying may be performed with heat at about 50° C. to about 70° C. for about 18 hours to about 36 hours.

For example, the ginseng may include fresh ginseng. For example, the ginseng may be fresh ginseng. When the ginseng is fresh ginseng, compared with white ginseng, red ginseng, black ginseng, etc., the content of the specific ginsenoside compound represented by Chemical Formula 1 may be significantly increased, when the method according to an embodiment is applied.

For example, in Chemical Formula 1, $R^1$ may be a C1 to C20 alkyl group substituted with a hydroxy group, $R^2$ and $R^8$ may each independently be a hydroxy group, $R^3$ to $R^7$ and $R^9$ may each independently be an unsubstituted C1 to C20 alkyl group, $R^{10}$ may be a C1 to C20 alkyl group substituted with a functional group represented by Chemical Formula 2, n1 may be an integer of 1, and n3 may be an integer of 3,

[Chemical Formula 2]

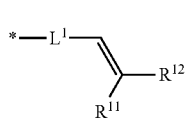

wherein, in Chemical Formula 2,
$L^1$ may be a substituted or unsubstituted C1 to C20 alkylene group, and
$R^{11}$ and $R^{12}$ may each independently be a hydrogen atom or a substituted or unsubstituted C1 to C20 alkyl group.

For example, Chemical Formula 1 may be represented by Chemical Formula 1-1.

[Chemical Formula 1]

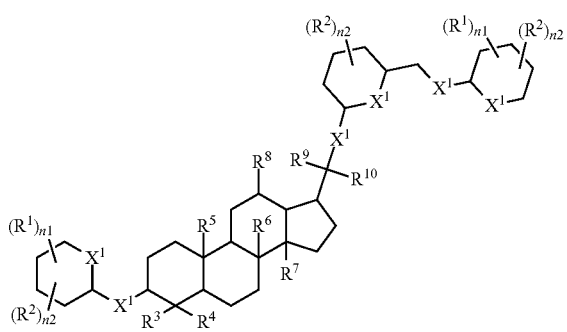

In Chemical Formula 1,
$X^1$ is an oxygen atom or a sulfur atom,
$R^1$ to $R^{10}$ are each independently a hydroxy group or a substituted or unsubstituted C1 to C20 alkyl group, and
n1 and n2 are each independently an integer of 0 to 4, provided that $1 \leq n1+n2 \leq 4$.

Chemical Formula 1 may be as described above.

Another embodiment provides a composition for enhancing a skin barrier including the anaerobic-naturally fermented ginseng extract as an active ingredient.

For example, the anaerobically fermented ginseng extract including the compound represented by Chemical Formula 1, based on a total amount of the composition for enhancing a skin barrier, may be included within a concentration range of about 1 μg/ml to about 100 mg/ml, for example about 1 μg/ml to about mg/ml, for example about 1 μg/ml to about 1 mg/ml, for example about 1 μg/ml to about 500 μg/ml, for example about 1 μg/ml to about 100 μg/ml, for example greater than or equal to about 1 μg/ml and less than or equal to about 100 μg/ml, less than or equal to about 90 μg/ml, less than or equal to about 80 μg/ml, less than or equal to about 70 μg/ml, less than or equal to about 60 μg/ml, less than or equal to about 50 μg/ml, less than or equal to about 40 μg/ml, less than or equal to about 30 μg/ml, less than or equal to about 20 μg/ml, or for example about 1 μg/ml to about 50 μg/ml.

[Chemical Formula 1-1]

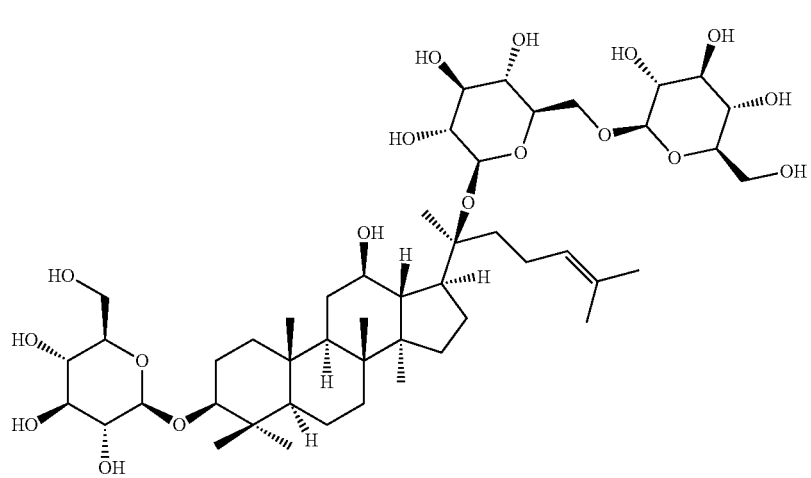

Another embodiment provides an anaerobic-naturally fermented ginseng extract including the compound represented by Chemical Formula 1 extracted by the aforementioned method.

For example, the compound represented by Chemical Formula 1, based on the total amount of the composition for enhancing a skin barrier, may be included within a concentration range of about 50 nmoles to about 5000 nmoles, for example greater than or equal to about 50 nmoles and less than or equal to about 5000 nmoles, less than or equal to about 4500 nmoles, less than or equal to about 4000 nmoles, less than or equal to about 3500 nmoles, less than or equal to about 3000 nmoles, less than or equal to about 2500 nmoles, less than or equal to about 2000 nmoles, less than or equal to about 1500 nmoles, less than or equal to about 1000 nmoles, or for example about 50 nmoles to about 2500 nmoles.

The composition for enhancing a skin barrier according to an embodiment includes the compound represented by Chemical Formula 1 and/or the anaerobically fermented ginseng extract including the same as an active ingredient within the concentration ranges, and thus may increase expression levels of genetic markers related to skin moisturizing and enhancing skin barriers such as Filaggrin (skin moisturizing index), Occludin (skin barrier index), and ATP-binding cassette sub-family A member 12 (ATP-binding cassette transporter 12; skin barrier index). Filaggrin is one of the main components of the cornified envelope (CE) and helps keratin filaments to aggregate with each other, wherein as the corresponding indicator increases, the skin moisturizing/barrier function may increase, and the Occludin is a protein involved in tight junctions, wherein when this protein marker is lacking, cell adhesion is weakened, causing aging and adversely affecting skin barriers. On the other hand, the ATP-binding cassette sub-family A member 12 (ATP-binding cassette transporter 12) plays an important role of forming essential lipids for skin barriers by transporting the lipids to a trans-Golgi network and lamellar granules, wherein as the corresponding indicator increases, the skin moisturizing/barrier function may increase.

Since the anaerobically fermented ginseng extract obtained in the method according to an embodiment, compared with a fresh ginseng extract, significantly increases the expression level of Filaggrin, and in addition, the three genetic indices significantly increase depending on a concentration of the compound represented by Chemical Formula 1 (in the anaerobically fermented ginseng extract), the compound represented by Chemical Formula 1 and/or the anaerobically fermented ginseng extracted in the method may be very suitable as an active ingredient of a composition for enhancing skin barriers.

It is possible to appropriately determine the dosage, application form, and formulation of the composition for enhancing skin barrier according to the embodiment according to the purpose of use. The form of application of the composition for enhancing a skin barrier is not particularly limited, and it can be applied both by inhalation and transdermally. The formulations may be any form, for example, perfumes, shampoos, conditioners, skin care, body shampoos, body conditioners, body powders, air fresheners, deodorants, bath agents, lotions, creams, soaps, toothpastes, cosmetics such as aerosol products, and other fragrances in general. It may also be used for medicines such as inhalation drugs.

In addition to the above essential ingredients, the composition for enhancing a skin barrier includes ingredients commonly used in skin external compositions for example, cosmetics and pharmaceuticals, for example whitening agents, moisturizing agents, antioxidants, oily ingredients, ultraviolet absorbers, surfactants, thickeners, alcohols, powder components, colorants, aqueous components, water, various skin nutrients, and the like may be appropriately blended as needed.

In addition, metal sequestering agents such as disodium edetate, trisodium edetate, sodium citrate, sodium polyphosphate, sodium metaphosphate, and gluconic acid, caffeine, tannin, verapamil, tranexamic acid and derivatives thereof, licorice extract, glabridean, a hot water extract of quince fruit, various crude drugs, drugs such as tocopherol acetate, glycyrrhizic acid, and derivatives thereof, or salts thereof, vitamin C, magnesium ascorbate phosphate, ascorbyl glucoside, arbutin, whitening agents such as kojic acid, sugars, such as glucose, fructose, mannose, sucrose, and trehalose, vitamin A such as retinoic acid, retinol, retinol acetate, and retinol palmitate, and the like may also be further included suitably.

For example, the composition for enhancing a skin barrier may be a cosmetic composition.

In the present specification "cosmetic" may refer to any material that may have a medical function in addition to the cosmetic function, as well as the cosmetic function.

The chemical formulation of the cosmetic composition is not particularly limited and may be appropriately selected as desired.

For example, the cosmetic composition may be formulated into chemical formulations such as solutions, suspend liquids, emulsions, pastes, gels, creams, lotions, powders, soaps, surfactant-containing cleansers, oils, powder foundations, emulsion foundations, wax foundations, and sprays, but is not limited thereto. More specifically, it may be formulated into cosmetic compositions such as detergents, tonics, hair dressings, nourishing lotions, essences, serums, treatments, conditioners, shampoos, lotions, wools, hair dyes, and the like, and may be formulated into basic cosmetics such as oil-in-water (O/W) type, a water-in-oil (W/O), and the like. For example, the composition may have one formulation selected from skin lotions, skin toners, astringents, lotions, milk lotions, moisture lotions, nourishing lotions, massage creams, nourishing creams, moisture creams, hand creams, ointments, foundations, essences, nourishing essences, packs, soaps, cleansing foams, cleansing lotions, cleansing creams, body lotions, body cleansers, gels, creams, patches, and sprays. In addition, in the composition, in addition to the above-mentioned essential components in each chemical formulation, other components may be appropriately selected and formulated without difficulty by a person of ordinary skill in the art according to types or use purposes of other external preparations. For example, ultraviolet (UV) blocking agents, hair conditioning agents, fragrances, and the like may be further included.

The cosmetic composition may include a cosmetically acceptable medium or base. These are all chemical formulations suitable for topical applications. The cosmetic composition may be provided in the forms of emulsions obtained by dispersing an oil phase in an aqueous phase, suspensions, microemulsions, microcapsules, microgranules, or ion-type (liposome) and/or non-ionized vesicle dispersing agents, or in the forms of creams, skins, lotions, powders, ointments, sprays, or concealment sticks. These compositions may be prepared according to conventional methods in the art.

When the chemical formulation of the present invention is a solution or emulsion, a solvent, a solubilizer, or an emulsifier may be used as a carrier component. For example, water, ethanol, isopropanol, ethyl carbonate, ethyl acetate, benzyl alcohol, benzyl benzoate, propylene glycol, 1,3-butylglycol oil, a glycerol aliphatic ester, a polyethylene glycol, or a fatty acid ester of sorbitan may be used.

If the chemical formulation of the present invention is used as a suspension, the carrier component may be a diluent of a liquid such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tracant, and the like.

If the chemical formulation of the present invention is pastes, creams, or gels, the carrier component may be an animal oil, a vegetable oil, wax, paraffin, starch, tracant, cellulose derivatives, polyethylene glycol, silicone, bentonite, silica, talc, or zinc oxide.

If the chemical formulation of the present invention is powders or sprays, the carrier component may be lactose, talc, silica, aluminum hydroxide, calcium silicate, or polyamide powders. Particularly, in the case of sprays, a propellant such as chlorofluorohydrocarbon, propane/butane, or dimethyl ether may be additionally included.

In an embodiment of the present invention, it may include thickeners in addition to the cosmetic composition. The thickeners included in the cosmetic composition of the present invention may be methyl cellulose, carboxyl methyl cellulose, carboxyl methyl hydroxy guanine, hydroxy methyl cellulose, hydroxyethyl cellulose, a carboxyl vinyl polymer, polyquaternium, cetearyl alcohol, stearic acid, and carrageenan. Preferably one or more of carboxyl methyl cellulose, a carboxyl vinyl polymer, and polyquaternium may be used, and most preferably a carboxyl vinyl polymer may be used.

In an embodiment of the present invention, the cosmetic composition may include a variety of suitable bases and additives as needed, and the types and amounts of these components may be easily selected by the inventor. If necessary, it may include an acceptable additive, and may further include, for example, conventional ingredients such as antiseptics, pigments, additives, and the like.

The antiseptics may be specifically phenoxyethanol or 1,2-hexanediol, and the fragrances may be artificial fragrances.

In an embodiment of the present invention, the cosmetic composition may include a composition selected from water-soluble vitamins, oil-soluble vitamins, polymeric peptides, polymeric polysaccharides, sphingolipids, and seaweed extracts. Other ingredients that may be added include fats and oils, humectants, emollients, surfactants, organic and inorganic pigments, organic powders, ultraviolet (UV) absorbers, antiseptics, fungicides, antioxidants, plant extracts, pH adjusters, alcohols, pigments, fragrances, blood circulation accelerators, coolants, anhidrotics, purified water, and the like.

In addition, the compounding components which may be added other than these are not particularly limited. Moreover, any component may be blended in a range which does not damage the purpose and effect of the invention.

Furthermore, the composition for enhancing a skin barrier according to an embodiment may be used as a pharmaceutical composition.

Advantages and features of the present invention and methods for achieving them will be apparent with reference to the examples described below in detail. One aspect of the present disclosure will be described in detail with reference to examples. However, these examples are specifically provided for describing the present invention, and the range of the present invention is not limited to these examples.

EXAMPLES

Preparation Example: Preparation of Fermented *Ginseng* Extract and Confirmation of the Compound Represented by Chemical Formula 1-1

Fresh ginseng was washed twice to three times, rolled for 30 minutes, cut/crushed into a size of 1 to 2 cm, sealed (at 50° C.), and then naturally fermented under an anaerobic condition for 3 weeks. Subsequently, the obtained ginseng was dried with hot air at 60° C., obtaining an anaerobic-naturally fermented ginseng extract.

The anaerobic-naturally fermented ginseng was repeatedly extracted once to three times in 50 to 80% EtOH for 1 to 5 hours at 50 to 80° C. The extracted sample was filtered under a reduced pressure with a Whatman No. 1 paper filter, concentrated with a vacuum rotary concentrator to remove solvent components, and purified, preparing an anaerobic-naturally fermented ginseng extract.

Furthermore, the anaerobic-naturally fermented ginseng extract was HPLC-analyzed under conditions of a column (Mightysil RP-18 GP C18), an ultraviolet absorbance detector (203 nm), an injection amount (10 uL), a flow rate (1.0 mL/min), and a mobile phase (D.I WATER, Acetonitrile), confirming that there was a compound represented by Chemical Formula 1-1 and other types of ginsenoside compounds. Specifically, various active substances such as a ginsenoside compound and the like were checked with respect to content changes for 28 days, and the results are shown in Tables 1 and 2.

[Chemical Formula 1-1]

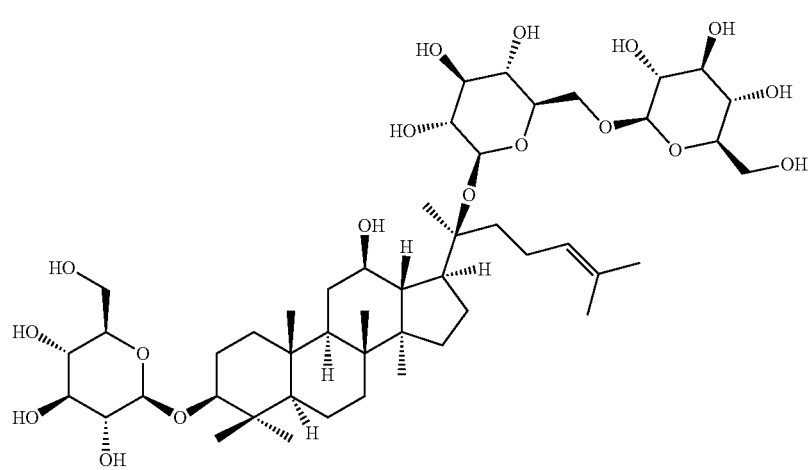

TABLE 1

| Component | | 0 hours | 48 hours | 72 hours | 168 hours | 14 days | 21 days | 28 days |
|---|---|---|---|---|---|---|---|---|
| PPD | Rb1 | 1637 | 3640 | 3894 | 4272 | 3564 | 1302 | 1743 |
| | Rb2 | 628 | 1608 | 1775 | 2048 | 1736 | 676 | 935 |
| | Rc | 832 | 1866 | 2089 | 2375 | 2008 | 728 | 1026 |
| | Rd | 232 | 706 | 856 | 1211 | 1140 | 580 | 837 |
| | Chemical Formula 1-1 | 228 | 1186 | 1914 | 4209 | 5523 | 7176 | 8970 |
| | C-O | 35 | 162 | 267 | 576 | 798 | 1092 | 1416 |
| | Mc1 | 34 | 139 | 231 | 508 | 717 | 1019 | 1310 |
| | GF2 | 8 | 55 | 97 | 234 | 363 | 584 | 778 |
| | Rg3 | 8 | 41 | 67 | 169 | 322 | 470 | 573 |
| | Rg5 | 0 | 10 | 17 | 63 | 136 | 229 | 278 |
| | Rk1 | 0 | 10 | 18 | 56 | 114 | 178 | 210 |

TABLE 2

| Component | | 0 hours | 48 hours | 72 hours | 168 hours | 14 days | 21 days | 28 days |
|---|---|---|---|---|---|---|---|---|
| PPT | Re | 3880 | 3123 | 3125 | 2857 | 2041 | 776 | 1015 |
| | Rf | 645 | 510 | 410 | 310 | 234 | 84 | 95 |
| | Rg1 | 2526 | 2159 | 2128 | 1966 | 1365 | 550 | 660 |
| | Rh1 | 16 | 186 | 281 | 507 | 730 | 958 | 1058 |
| | Rg2 | 202 | 201 | 219 | 296 | 413 | 485 | 587 |
| | GF1 | 6 | 40 | 48 | 78 | 93 | 99 | 125 |
| Oleanane | Ro | 463 | 457 | 465 | 411 | 423 | 396 | 383 |

Referring to Tables 1 and 2, according to the method of an embodiment, a content of the compound represented by Chemical Formula 1-1 increased with time. In other words, the method of an embodiment turned out to greatly increase the content of the compound represented by Chemical Formula 1-1 in the anaerobic-naturally fermented ginseng extract.

Experimental Example 1: Comparison of Content of Main Ginsenoside Compounds Between Anaerobic-Naturally Fermented *Ginseng* Extract and Fresh *Ginseng* Extract The anaerobic-naturally fermented ginseng extract according to the preparation example and an unfermented fresh ginseng extract were HPLC-analyzed under the same conditions to check a content of main ginsenoside compounds in each extract, and the results are shown in Table 3 and FIG. 2.

TABLE 3

(unit: %)

| | Anaerobic-naturally fermented ginseng extract | Unfermented fresh ginseng extract |
|---|---|---|
| Chemical Formula 1-1 | 9.99 | <0.1 |
| Rb1 | 8.97 | 0.80 |
| Rb2 | 6.62 | 0.36 |
| Rb3 | 0.79 | 0.06 |
| Rc | 6.08 | 0.47 |
| Rd | 3.35 | 0.03 |
| Re | 3.86 | 0.72 |
| Rg1 | 2.77 | 0.30 |

Figure 2:
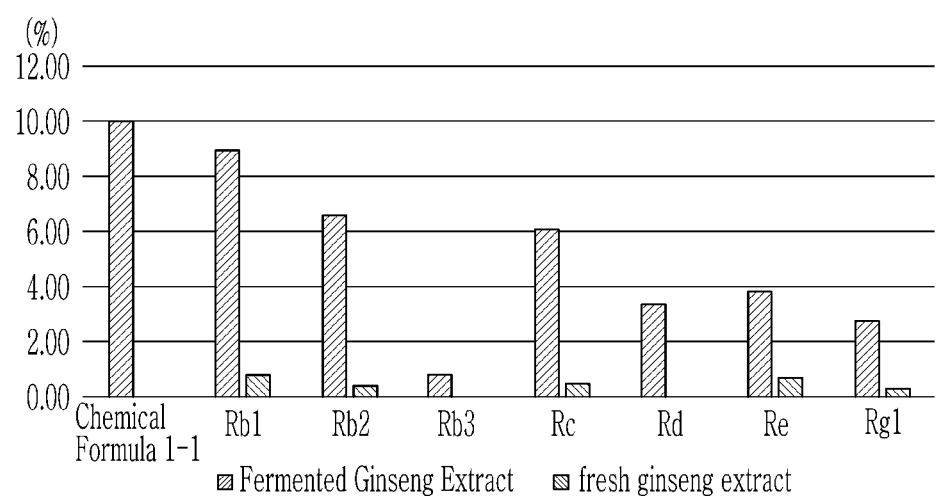
FIG. 2 is a graph showing contents of the main ginsenoside substances in the anaerobically fermented ginseng extract and unfermented fresh ginseng extract according to an embodiment.

Referring to Table 3 and FIG. 2, the anaerobic-naturally fermented ginseng extract according to the method of an embodiment turned out to contain more of the compound represented by Chemical Formula 1-1 than other ginsenoside compounds.

Experimental Example 2: Comparison of Contents of Compound Represented by Chemical Formula 1-1 According to Presence or Absence of Rolling The anaerobic-naturally fermented ginseng extract of the preparation example and the same anaerobic-naturally fermented ginseng extract as the preparation example except for not rolling were HPLC analyzed under the same conditions as above to check contents of main ginsenoside compounds in each extract, and the results are shown in Table 4.

TABLE 4

(unit: µg/g)

| | Anaerobic-naturally fermented ginseng extract (rolling is performed) | Anaerobic-naturally fermented ginseng extract (rolling is not performed) |
|---|---|---|
| Chemical Formula 1-1 | 2502 | 875 |

Referring to Table 4, when the rolling was performed, compared with when the rolling was not performed, the content of the compound represented by Chemical Formula 1-1 was significantly increased.

Experimental Example 3: Comparison Between Anaerobic and Aerobic Conditions

Figure 3:
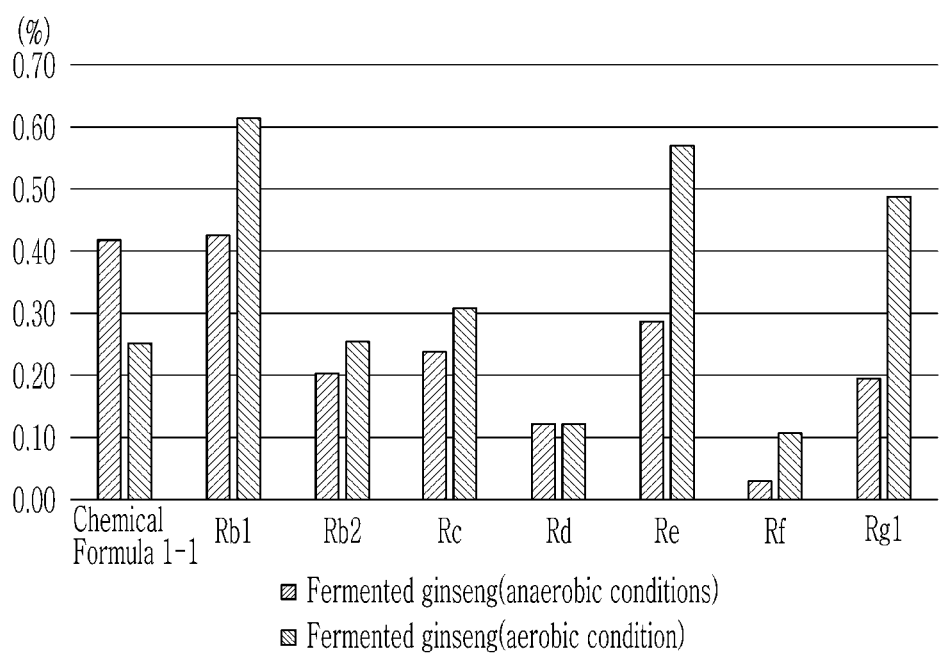
FIG. 3 is a graph showing contents of the main ginsenoside substances of the anaerobically fermented ginseng extract and aerobically fermented ginseng extract according to an embodiment.

The anaerobic-naturally fermented ginseng extract of the preparation example and an aerobic-naturally fermented ginseng extract under the same conditions except for under an aerobic condition instead of the anaerobic condition in the preparation example were HPLC-analyzed to check contents of main ginsenoside compounds in each extract, and the results are shown in Table 5 and FIG. 3.

TABLE 5

(unit: %)

|  | Anaerobic-naturally fermented ginseng extract | Aerobic-naturally fermented ginseng extract |
|---|---|---|
| Chemical Formula 1-1 | 10.42 | 0.25 |
| Rb1 | 0.43 | 0.61 |
| Rb2 | 0.20 | 0.25 |
| Rc | 0.24 | 0.31 |
| Rd | 0.12 | 0.12 |
| Re | 0.29 | 0.57 |
| Rg1 | 0.20 | 0.49 |

Referring to Table 5 and FIG. 3, when naturally fermented under an anaerobic condition, compared with when naturally fermented under an aerobic condition, the content of the compound represented by Chemical Formula 1-1 alone was significantly increased.

Experimental Example 4: Preparation of Composition for Enhancing Skin Barrier

The anaerobic-naturally fermented ginseng extract of the preparation example and an unfermented fresh ginseng extract were used in compositions shown in Table 6 to prepare each cosmetic composition for enhancing skin barriers. Purified water was used, when mixed with other components, to reach 100 wt % of a total weight of the cosmetic composition.

TABLE 6

(unit: ppm)

|  | Example 1 | Comparative Example 1 |
|---|---|---|
| Purified water | Balance | Balance |
| EDTA-2Na | 0.05 | 0.05 |
| Lauric acid | 5 | 5 |
| Myristic acid | 7 | 7 |
| Palmitic acid | 1 | 1 |
| KOH | 7.9 | 7.9 |
| Guar hydroxypropyl trimonium chloride | 0.5 | 0.5 |
| Polyquaternium-7 | 3.0 | 3.0 |
| Anaerobic-naturally fermented ginseng extract | 5.0 | — |
| Unfermented fresh ginseng extract | — | 5.0 |
| Disodium cocoamphodiacetate | 1.0 | 1.0 |

Referring to Table 6, it was possible to use the anaerobic-naturally fermented ginseng extract according to an embodiment to prepare a cosmetic composition for enhancing skin barriers.

Figure 4:
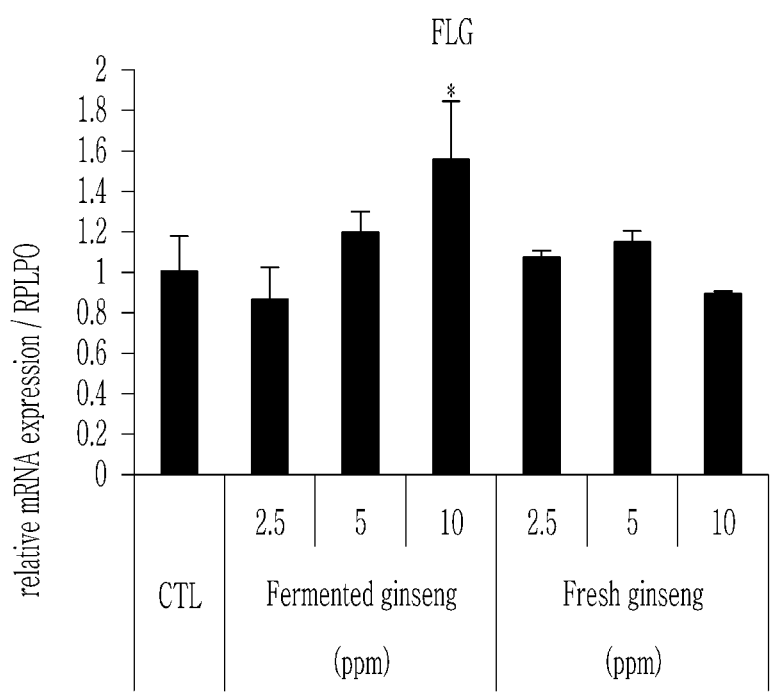
FIG. 4 is a graph showing an expression level of a Filaggrin gene according to each concentration change of an anaerobically fermented ginseng extract according to an embodiment and an unfermented fresh ginseng extract in compositions respectively including the extracts as an active ingredient.

Test Example 5: Confirmation of Skin Barrier Enhancing Function (1) Normal human epidermal keratinocytes (NHEK) were cultured in 6-well culture media. The anaerobic-naturally fermented ginseng extract of the preparation example and an unfermented fresh ginseng extract were respectively added to the NHEK media and cultured. After harvesting the cells on the $4^{th}$ day, separating RNA therefrom, and synthesizing cDNA through RT-PCR (reverse transcriptional polymerase chain reaction), the synthesized cDNA was measured with respect to an expression level of the Filaggrin gene through Taqman real-time PCR, and the results are shown in FIG. 4. Referring to FIG. 4, the anaerobic-naturally fermented ginseng extract of the preparation example exhibited an increased expression level of the Filaggrin (FLG) gene, as a concentration thereof was increased, but the unfermented fresh ginseng extract exhibited that the expression level of Filaggrin (FLG) gene did not significantly increase regardless of a concentration thereof, which shows that the anaerobic-naturally fermented ginseng extract of the preparation example improved skin barriers.

Figure 5:
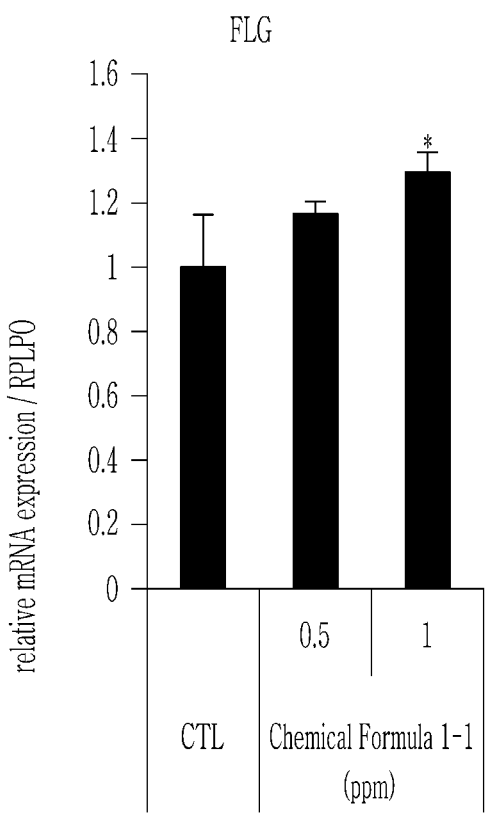
FIG. 5 is a graph showing an expression level of the Filaggrin (FLG) gene according to a concentration change of a compound represented by Chemical Formula 1-1 as an active ingredient in a composition including the same.
Figure 6:
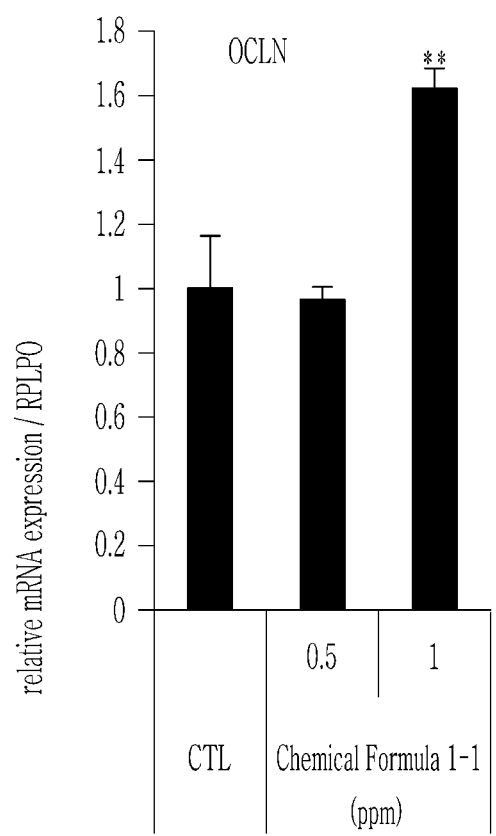
FIG. 6 is a graph showing an expression level of an Occludin (OCLN) gene according to a concentration change of the compound represented by Chemical Formula 1-1 as an active ingredient in the composition including the same.
Figure 7:
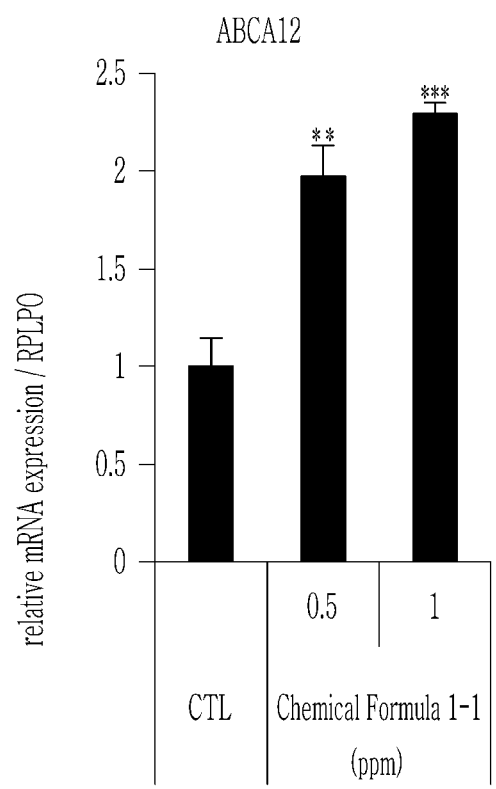
FIG. 7 is a graph showing an expression level of an ATP-binding cassette sub-family A member 12 (ATP-binding cassette transporter 12; ABCA12) gene according to a concentration change of the compound represented by Chemical Formula 1-1 as an active ingredient in the composition including the same.

(2) The compound represented by Chemical Formula 1-1, which was separated from the anaerobic-naturally fermented ginseng extract of the preparation example, was added to an NHEK culture media and treated in the same manner as in (1), and then measured with respect to each gene expression level of Filaggrin, Occludin, and ATP-binding cassette subfamily A member 12 (ATP-binding cassette transporter 12), and the results are shown in FIGS. 5 to 7. Referring to FIGS. 5 to 7, the compound represented by Chemical Formula 1-1 exhibited that each gene expression level of Filaggrin (FLG), Occludin (OCLN), and ATP-binding cassette subfamily A member 12 (ATP-binding cassette transporter 12; ABCA12) increased, as a concentration thereof was increased, which shows that the compound represented by Chemical Formula 1-1 improved skin barriers.

Although the preferred embodiments of the present invention have been described in detail, the scope of the present invention is not limited thereto, and various modifications and improvements by those skilled in the art using the basic concept of the present invention defined in the following claims are also within the scope of the invention.

What is claimed is:

1. A method for extracting a compound of Chemical Formula 1-1 from ginseng, comprising:
   anaerobic natural fermentation of ginseng without an inoculation of microorganisms,

[Chemical Formula 1-1]

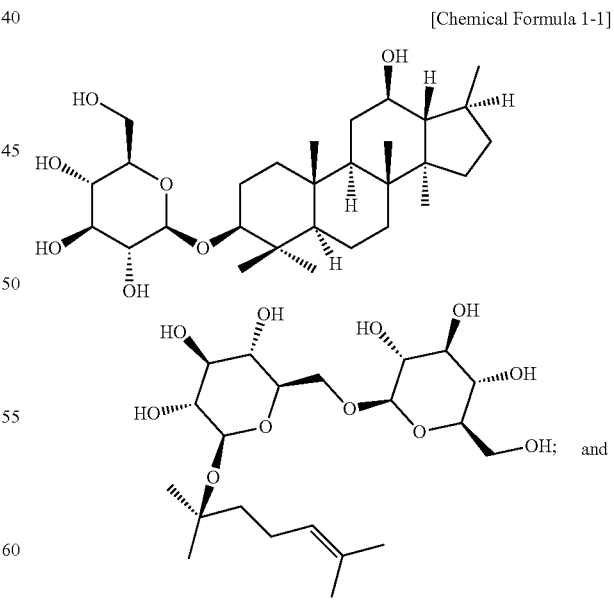

wherein the ginseng is subjected to rolling.

2. The method of claim 1, wherein
the natural fermentation is fermentation for about 15 days to about 30 days at about 35° C. to about 65° C.

3. The method of claim 1, wherein
the natural fermentation is fermentation of the ginseng in a sealed state.

4. The method of claim 1, wherein
the rolling is performed for about 20 minutes to about 60 minutes.

5. The method of claim 1, wherein
the method includes:
washing ginseng;
rolling the washed ginseng;
cutting and/or crushing the rolled ginseng;
naturally fermenting the cut and/or crushed ginseng without inoculating microorganisms;
drying the naturally fermented ginseng; and
extracting the dried naturally fermented ginseng to obtain an extract containing the compound of Chemical Formula 1-1.

6. The method of claim 1, wherein
the ginseng includes fresh ginseng.

* * * * *